(12) United States Patent
Merker et al.

(10) Patent No.: US 8,390,988 B2
(45) Date of Patent: Mar. 5, 2013

(54) MONOMERS OF SELECTED COLOUR NUMBERS AND CAPACITORS PREPARED THEREFROM

(75) Inventors: Udo Merker, Köln (DE); Klaus Wussow, Netphen (DE); Knud Reuter, Krefeld (DE); Andreas Elschner, Mülheim (DE)

(73) Assignee: Heraeus Precious Metals GmbH & Co. KG (DE)

(*) Notice: Subject to any disclaimer, the term of this patent is extended or adjusted under 35 U.S.C. 154(b) by 132 days.

(21) Appl. No.: 12/894,976

(22) Filed: Sep. 30, 2010

(65) Prior Publication Data
US 2011/0102970 A1 May 5, 2011

(30) Foreign Application Priority Data

Sep. 30, 2009 (CN) .......................... 2009 1 0258419
Sep. 30, 2009 (EP) ...................... 09012373

(51) Int. Cl.
*H01G 9/00* (2006.01)
(52) U.S. Cl. ........ 361/523; 361/528; 361/516; 361/519; 361/517; 361/525
(58) Field of Classification Search .................. 361/525, 361/516–519, 523, 528–529, 530, 540–541, 361/500–512; 29/25.01, 25.03
See application file for complete search history.

(56) References Cited

U.S. PATENT DOCUMENTS

| | | | |
|---|---|---|---|
| 2,453,103 A | 11/1948 | Turnbull, Jr. | |
| 6,136,176 A | 10/2000 | Wheeler et al. | |
| 6,154,358 A * | 11/2000 | Fukaumi et al. | 361/523 |
| 6,215,651 B1 * | 4/2001 | Takada et al. | 361/523 |

(Continued)

FOREIGN PATENT DOCUMENTS

| | | |
|---|---|---|
| EP | 1 142 888 A1 | 10/2001 |
| EP | 1 860 111 A1 | 11/2007 |

OTHER PUBLICATIONS

E. Campaigne et al., "3-Sbustituted Thiophenes", J. Am. Chem. Soc., vol. 77, No. 20, pp. 5365-5369, 1955.

(Continued)

*Primary Examiner* — Nguyen T Ha
(74) *Attorney, Agent, or Firm* — Novak Druce Connolly Bove + Quigg LLP

(57) ABSTRACT

The disclosure describes a monomer having the general formula (I):

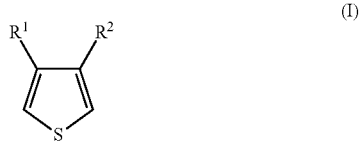

(I)

in which $R^1$ and $R^2$ stand, independently of one another, for hydrogen, for an optionally substituted $C_1$-$C_{20}$-alkyl group or $C_1$-$C_{20}$-oxyalkyl group, optionally interrupted by 1 to 5 oxygen atoms and/or sulfur atoms, or jointly for an optionally substituted $C_1$-$C_{20}$-dioxyalkylene group or $C_6$-$C_{20}$-dioxyarylene group. The monomer has a color in a range of a Hazen color number determined according to test method described herein of at least 20 to a Gardner color number determined according to test method described herein of not more than 5. The present invention also relates to a method for the manufacture of a capacitor, a capacitor obtained by this method and to the use of a monomer.

16 Claims, 1 Drawing Sheet

U.S. PATENT DOCUMENTS

| | | | |
|---|---|---|---|
| 6,334,966 B1 | 1/2002 | Hahn et al. | |
| 6,369,239 B2 | 4/2002 | Rauchschwalbe et al. | |
| 6,562,255 B1 * | 5/2003 | Feger | 252/62.2 |
| 7,004,983 B2 * | 2/2006 | Honda et al. | 29/25.03 |
| 7,449,588 B2 | 11/2008 | Jonas et al. | |
| 8,023,250 B2 * | 9/2011 | Ning et al. | 361/516 |

OTHER PUBLICATIONS

Igor F. Perepichka et al., "Electronic Properties and Reactivity of Short-Chain Oligomers of 3,4-Phenylenedioxythiophene (PheDOT)", Chem. Eur. J., vol. 12, pp. 2960-2966, 2006.

John S. Jomas et al., Database Accession No. BRN 9042389, XP-002559263, pp. 216-224, 2002.

M. Coffey et al., Database Accession No. BRN 7126466, XP-002559264, pp. 2205-2212, 1996.

Vishay Sprague, "Solid Tantalum Chip Capacitors", www.vishay.com, Product Description, XP-002559262, p. 15, Jun. 27, 2008.

Wilhelm Steinkopf et al., "Studien in der Thiophenreihe", Justus Liebigs Annalen Der Chemie, vol. 533, No. 1, pp. 264-269, 1938.

Partial European Search Report from corresponding European Application No. EP 09 01 2373 dated Dec. 8, 2009.

Chinese Examination Report dated Nov. 22, 2012 from Chinese counterpart application.

Roquet et al., 3,4-Phenylenedioxythiophene (PheDOT): a novel platform for the synthesis of planar substituted π-donor conjugated ystems, J. Mater.Chem., vol. 14, No. 9, pp. 1396-1400.

\* cited by examiner

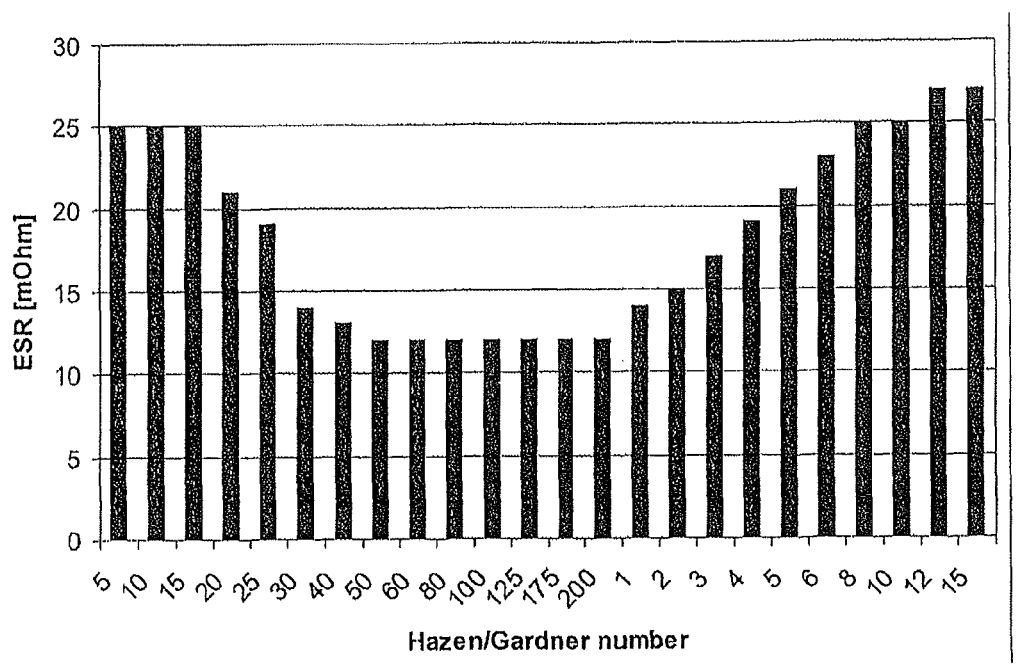

MONOMERS OF SELECTED COLOUR NUMBERS AND CAPACITORS PREPARED THEREFROM

The invention relates to a monomer being characterized by selected colour numbers, to a method for the manufacture of a capacitor, a capacitor obtained by this method and to the use of a monomer.

Solid electrolytic capacitors with conductive polymers as the cathode materials have been widely used in the electronics industry due to their advantageously low equivalent series resistance (ESR) and "non-burning/non-ignition" failure mode. Various types of conductive polymers including polypyrrole, polyaniline, and poly(3,4-ethyldioxythiophene) (PEDOT) are applied to electrolytic capacitors as a cathode material when valve metals such as Ta, Al, and Nb as well as conductive oxides such as ceramic NbO, are used as the anode. In a manufacturing process to produce conductive polymer based valve metal capacitors, Ta powder, for example, is mechanically pressed to form Ta metal pellets, which are subsequently sintered at high temperature under vacuum. The sintered pellets are anodized in an electrolyte solution to form a dielectric layer ($Ta_2O_5$) on the anode surface. Following that, multiple layers of a conductive polymer, such as poly 3,4-ethylenedioxythiophene (PEDOT), are laid down by a multiple dipping polymerization process. During the polymerization process, an oxidant solution, such as iron (III) p-toluenensulfonate solution in a solvent, is in some cases first applied onto the anodes. It is then followed by the application of a liquid monomer or monomer solution as disclosed by D Wheeler, et al in U.S. Pat. No. 6,136,176 and by R. Hahn, et al., in U.S. Pat. No. 6,334,966.

For the purpose of achieving high electrical conductivities in this connection, the purity of the thiophene derivatives monomers used for the preparation of the conductive polymer plays a crucial role. Ordinarily, distillation is used as a conventional purification process for thiophene derivatives.

As disclosed in EP 1 860 111 A1 thiophenes that have been purified in this way have a tendency in the course of storage towards changes in colour and/or the formation of undesirable secondary components, such as, for example, the formation of dimers. This results in considerable impairment of the properties of the polythiophenes prepared therefrom. In order to avoid these negative effects of thiophene derivative dimers EP 1 860 111 A1 discloses to pre-treat the thiophene derivatives with alkaline materials.

The state of the art therefore suggests using thiophenes which are as clear as possible, obtained either by freshly distilling thiophenes or by pre-treating thiophenes with alkaline materials preferably directly before they are used for the manufacture of electronic capacitors, by means of which any coloration can be inhibited. The state of the art explicitly suggests using thiophenes which are as pure and thus as clear as possible.

It has been observed, however, that using freshly distilled thiophenes for the manufacture of electronic capacitors, which do not show any coloration, leads to capacitors having unfavourably high ESR-values.

An object of the present invention is thus to reduce or even overcome the disadvantages of the state of the art.

In particular it is an object of the present invention to provide a monomer based on a thiophene derivative that can be used for the manufacture of electronic capacitors, in particular by means of in situ polymerization, wherein in a reproducible manner capacitors with low ESR-values can be obtained.

It is furthermore an object of the present invention to provide a process for the manufacture of a capacitor with reproducible low ESR-values.

It is also an object of the present invention that while the ESR-values are lowered, the capacitance, as an important parameter with regard to the performance of the capacitor is not harmed.

A contribution to the solution of at least one of the above objects is provided by the subject matters of the category-forming independent principal and adjacent claims, whereby the therefrom dependent sub-claims represent preferred embodiments of the present invention, whose subject matters likewise make a contribution to solving at least one object.

The invention relates to a monomer having the general formula (I)

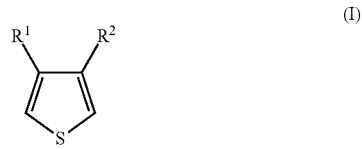

(I)

in which
$R^1$ and $R^2$ stand, independently of one another, for hydrogen, for an optionally substituted $C_1$-$C_{20}$-alkyl group or $C_1$-$C_{20}$-oxyalkyl group, optionally interrupted by 1 to 5 oxygen atoms and/or sulfur atoms, or jointly for an optionally substituted $C_1$-$C_{20}$-dioxyalkylene group or $C_6$-$C_{20}$-dioxyarylene group,
  wherein the monomer has a colour in a range of
    a Hazen colour number determined according to test method described herein of at least 20,
    and
    a Gardner colour number determined according to test method described herein of not more than 5.

The coloration of the monomer is preferably based on reaction products formed from the monomers, preferably of reaction products of the monomer that are metabolites of the monomer.

Surprisingly, it has now been found that using thiophenes which are almost completely clear, such as freshly distilled thiophenes, for the manufacture of electronic capacitors is disadvantageous as the ESR of such capacitors is quiet high. If, however, thiophenes are used that are characterized by a certain degree of coloration, the ESR can be significantly lowered.

Thiophene derivatives within the scope of the invention are preferably those having the general formula (II),

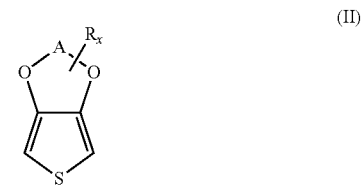

(II)

in which
A stands for an optionally substituted $C_1$-$C_5$-alkylene residue or a $C_6$-$C_{14}$-arylene residue, preferably for an optionally substituted $C_2$-$C_3$-alkylene residue,
R stands for a linear or branched, optionally substituted $C_1$-$C_{18}$-alkyl residue, preferably a linear or branched, optionally substituted $C_1$-$C_{14}$-alkyl residue, an optionally substituted $C_5$-$C_{12}$-cycloalkyl residue, an optionally substituted $C_6$-$C_{14}$-aryl residue, an optionally substituted $C_7$-$C_{18}$-aralkyl residue, an optionally substituted $C_1$-$C_4$-hydroxyalkyl residue, preferably an optionally substituted $C_1$-$C_2$-hydroxyalkyl residue, or a hydroxyl residue, x stands for an integer from 0 to 8, preferably from 0 to 6, particularly preferably for 0 or 1, and in the case where several residues R are bonded to A, these may be the same or different.

The general formula (II) is to be understood in such a way that x substituents R equal or different may be bonded to the alkylene residue or arylene residue A.

Particularly preferred thiophene derivatives within the scope of the invention are those having the general formula (IIa)

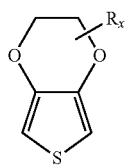

in which R and x have the significance stated for general formula (II).

In a preferred embodiment of the invention the thiophene derivative is 3,4-ethylenedioxythiophene.

$C_1$-$C_5$-alkylene residues A within the scope of the invention are methylene, ethylene, n-propylene, n-butylene or n-pentylene. $C_6$-$C_{14}$-arylene residues A within the scope of the invention may be, for example, phenylene, naphthylene or anthracenylidene. $C_1$-$C_{18}$ alkyl within the scope of the invention stands for linear or branched $C_1$-$C_{18}$-alkyl residues, such as, for example, methyl, ethyl, n-propyl, isopropyl, n-butyl, isobutyl, sec-butyl, tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadcyl or noctadecyl. $C_1$-$C_{20}$-alkyl groups furthermore include, for example, n-nonadecyl and n-eicosyl. $C_5$-$C_{12}$ cycloalkyl within the scope of the invention stands for $C_5$-$C_{12}$-cycloalkyl residues, such as, for example, cyclopentyl, cyclohexyl, cycloheptyl, cyclooctyl, cyclononyl or cyclodecyl; $C_5$-$C_{14}$ aryl for $C_5$-$C_{14}$-aryl residues, such as, for example, phenyl or naphthyl; and $C_7$-$C_{18}$ aralkyl for $C_7$-$C_{18}$-aralkyl residues, such as, for example, benzyl, o-tolyl, m-tolyl, p-tolyl, 2,3-xylyl, 2,4-xylyl, 2,5-xylyl, 2,6-xylyl, 3,4-xylyl, 3,5-xylyl or mesityl. $C_1$-$C_{20}$ oxyalkyl within the scope of the invention stands for $C_1$-$C_{20}$-oxyalkyl residues, such as, for example, methoxy, ethoxy, n-propoxy, isopropoxy, n-butoxy, isobutoxy, sec-butoxy, tert-butoxy, n-pentyloxy, 1-methylbutyloxy, 2-methylbutyloxy, 3-methylbutyloxy, 1-ethylpropyloxy, 1,1-dimethylpropyloxy, 1,2-dimethylpropyloxy, 2,2-dimethylpropyloxy, n-hexyloxy, n-heptyloxy, n-octyloxy, 2-ethylhexyloxy, n-nonyloxy, n-decyloxy, n-undecyloxy, n-dodecyloxy, n-tridecyloxy, n-tetradecyloxy, n-hexadcyloxy, n-nonadecyloxy or n-eicosyloxy. The preceding list serves for exemplary elucidation of the invention and is not to be regarded as being definitive.

Numerous organic groups enter into consideration as optionally further substituents of the alkylene residues or arylene residues A; for example, alkyl, cycloalkyl, aryl, halogen, ether, thioether, disulfide, sulfoxide, sulfone, sulfonate, amino, aldehyde, keto, carboxylic-ester, carboxylic-acid, carbonate, carboxylate, cyano, alkylsilane, alkoxysilane and carboxylamide groups.

To the extent that the thiophene derivative exhibits one or more stereocentres, the thiophene derivative may be a racemate, an enantiomerically pure or diastereomerically pure compound, or an enantiomerically enriched or diastereomerically enriched compound. The expression "enantiomerically enriched compound" is to be understood to mean a compound with an enantiomeric excess (ee) of more than 50%. The expression 'diastereomerically enriched compound' is to be understood to mean a compound with a diastereomeric excess (de) of more than 30%. According to the invention, however, it may also be a question of an arbitrary mixture of diastereomers.

The thiophene derivatives having the general formula (I), (II), or (IIa) are capable of being prepared by processes known to a person skilled in the art. Such a preparation process is described in EP-A-1 142 888, for example.

With respect to the colour number of the monomer according to the present invention it is especially preferred that the range is from a Hazen colour number determined according to the test method described herein of at least 20, preferably at least 25, even more preferably at least 30, even more preferably at least 40 and most preferably at least 50. Furthermore it is especially preferred with respect to the range that the Gardner colour number determined according to the test method described herein is not more than 5, preferably not more than 4, even more preferably not more than 3, even more preferably not more than 2 and most preferably not more than 1.

According to a first preferred embodiment of the monomer according to the present invention the range is from a Hazen colour number determined according to the test method described herein of at least 25 to a Gardner colour number determined according to the test method described herein of not more than 4.

According to a second preferred embodiment of the monomer according to the present invention the range is from a Hazen colour number determined according to the test method described herein of at least 30 to a Gardner colour number determined according to the test method described herein of not more than 3.

According to a third preferred embodiment of the monomer according to the present invention the range is from a Hazen colour number determined according to the test method described herein of at least 30 to a Gardner colour number determined according to the test method described herein of not more than 2.

According to a fourth preferred embodiment of the monomer according to the present invention the range is from a Hazen colour number determined according to the test method described herein of at least 30 to a Gardner colour number deter-according to the test method described herein of not more than 1.

According to a fifth preferred embodiment of the monomer according to the present invention the range is from a Hazen colour number determined according to the test method described herein of at least 50 to of not more than 200.

The monomer according to the present invention can be contained in a closed container. As containers, bottles, vessels and barrels a preferred. The inner volume of these containers is preferably at least 50 ml, more preferably at least 100 ml and most preferably at least 1000 ml. It is furthermore preferred that the bottle can be closed by means of a screw top. Moreover, the container can be a glass container, a plastic container or a metal container. Furthermore, the container is preferably impermeable for light, preferably for UV-light.

The present invention also relates to a method of forming a capacitor comprising forming an anode of a valve metal;

forming a precursor comprising said anode and a dielectric;

adding an intrinsically conductive polymer on said precursor, wherein said intrinsically conductive polymer is based on the monomer according to the invention.

In addition to the dielectric and the anode, the precursor may comprise one or more further layers. According to one embodiment of the present invention, application of the monomer according to the invention to the precursor can be effected directly on the dielectric or using an adhesion promoter, for example a silane, for example organofunctional silanes or hydrolysates thereof, e.g. 3-glycidoxypropyltrialkoxysilane, 3-aminopropyltriethoxysilane, 3-mercaptopropyltrimethoxysilane, 3-methacryloyloxypropyltrimethoxysilane, vinyltrimethoxysilane or octyltriethoxysilane, and/or one or more other functional layers. The intrinsically conductive polymer is then based on the monomer according to the invention if the polymer is mainly formed by polymerizing the monomers according to the present invention.

In a first step an anode is formed of a valve metal, wherein a valve metal powder with a high surface area is compressed and sintered to a porous electrode body. When this is done, an electrical contact wire, preferably of a valve metal, for example tantalum, is typically also compressed into the electrode body. It is alternatively also possible to etch metal foils in order to obtain a porous film. In the case of a wound capacitor, a porous anode film which forms the electrode body and a cathode film are separated by a separator and wound up.

Valve metals are understood within the scope of the invention to denote those metals whose oxide layers do not permit current to flow equally in both directions. When a voltage is applied to the anode the oxide layers of the valve metals prevent the flow of current, whereas when a voltage is applied to the cathode large currents flow that can destroy the oxide layer. Valve metals include Be, Mg, Al, Ge, Si, Sn, Sb, Bi, Ti, Zr, Hf, V, Nb, Ta and W as well as an alloy or compound of at least one of these metals with other elements. The best known examples of valve metals are Al, Ta and Nb. Compounds with comparable properties are those exhibiting metallic conductivity that can be oxidised and whose oxide layers have the properties described hereinbefore. For example NbO exhibits metallic conductivity, but is generally not regarded as a valve metal. Layers of oxidised NbO however exhibit the typical properties of valve metal oxide layers, so that NbO or an alloy or compound of NbO with other elements are typical examples of such compounds with comparable properties.

Consequently the term "oxidisable metal" covers not only metals but also an alloy or compound of a metal with other elements, provided that they exhibit metallic conductivity and can be oxidised.

The present invention accordingly particularly preferably provides a process for forming capacitors, which is characterised in that the valve metal or the compound with comparable properties is tantalum, niobium, aluminium, titanium, zirconium, hafnium, vanadium, an alloy or compound of at least one of these metals with other elements, NbO or an alloy or compound of NbO with other elements.

In a second step, a precursor comprising said anode and a dielectric is formed.

The dielectric is preferably formed on said anode. The dielectric preferably consists of an oxide of the electrode material or—in the case where this is already an oxide—of a higher oxidised form of the electrode material. The dielectric optionally contains further elements and/or compounds. The oxidisable metals are for example sintered in powder form to form a porous electrode body or a porous structure is impressed on a metallic body. The latter procedure may be carried out for example by etching a film. The porous electrode bodies are for example oxidised in a suitable electrolyte, such as for example phosphoric acid, by applying a voltage such that such a so called "oxidised electrode body" is obtained. The magnitude of this forming voltage depends on the oxide layer thickness to be achieved or on the subsequent application voltage of the capacitor. Preferred voltages are 1 to 300 V, particularly preferably 1 to 80 V.

In a third step of one embodiment of the present invention, the precursor is coated with a solution of the monomer as described above in order to deposit a conductive polymer by means of oxidative or electrochemical polymerization, preferably by means of oxidative polymerization using appropriate oxidising agents. In this context in one alternative according to the present invention it is preferred that the monomer according to the present invention is used as it is, i.e. with the colour numbers indicated above. It is especially preferred that the monomer, before it is used for the manufacture of the electronic capacitor, is not purified in such a way that the Hazen or Gardner colour number is lowered.

Optionally further layers, for example polymeric outer layer are applied. A coating containing good conducting layers, such as graphite and silver, or a metallic cathode body, serves as electrode for the discharge of the current. Finally the capacitor is contacted and encapsulated.

As oxidising agents there may be used all suitable metal salts known to the person skilled in the art for the oxidative polymerisation of thiophenes.

Metal salts suitable as oxidising agent are metal salts of main group metals or subgroup metals, the latter hereinafter also being termed transition metal salts, of the Periodic System of the Elements. Suitable transition metal salts are in particular salts of an inorganic or organic acid or of an inorganic acid comprising organic radicals, of transition metals such as for example iron(III), copper(II), chromium(VI), cerium(IV), manganese(IV) and manganese(VII) and ruthenium (III).

Preferred transition metal salts are those of iron(III). Conventional iron(III) salts are advantageously inexpensive, readily obtainable and are easy to handle, such as for example iron(III) salts of inorganic acids, such as for example iron(III) halides (e.g. $FeCl_3$) or iron(III) salts of other inorganic acids, such as $Fe(ClO_4)_3$ or $Fe_2(SO_4)_3$, and iron(III) salts of organic acids and of inorganic acids comprising organic radicals.

As iron(III) salts of inorganic acids comprising organic radicals, there may for example be mentioned iron(III) salts of sulfuric acid monoesters of $C_1$-$C_{20}$-alkanols, e.g. the iron (III) salt of lauryl sulfate.

Particularly preferred transition metal salts are those of an organic acid, in particular iron(III) salts of organic acids.

As iron(III) salts of organic acids, the following may for example be mentioned: iron(III) salts of $C_1$-$C_{20}$-alkanesulfonic acids, such as methanesulfonic, ethanesulfonic, propanesulfonic, butanesulfonic or higher sulfonic acids such as dodecanesulfonic acid, of aliphatic perfluorosulfonic acids, such as trifluoromethanesulfonic acid, perfluorobutanesulfonic acid or perfluorooctanesulfonic acid, of aliphatic $C_1$-$C_{20}$-carboxylic acids such as 2-ethylhexylcarboxylic acid, of aliphatic perfluorocarboxylic acids such as trifluoroacetic acid or perfluorooctanoic acid, and of aromatic sulfonic acids optionally substituted by $C_1$-$C_{20}$-alkyl groups, such as benzenesulfonic acid, o-toluenesulfonic acid, p-toluenesulfonic acid or dodecylbenzenesulfonic acid, and of cycloalkanesulfonic acids such as camphorsulfonic acid.

Arbitrary mixtures of these aforementioned iron(III) salts of organic acids may also be used as oxidising agent.

The use of iron(III) salts of organic acids and of inorganic acids comprising organic radicals has the great advantage that they do not have a corrosive effect.

Most particularly preferred as metal salts are iron(III) p-toluenesulfonate, iron(III) o-toluenesulfonate or a mixture of iron(III) p-toluenesulfonate and iron(III) o-toluenesulfonate.

Further suitable oxidising agents are peroxo compounds such as peroxodisulfates (persulfates), in particular ammonium and alkali metal peroxodisulfates, such as sodium and potassium peroxodisulfate, or alkali metal perborates—optionally in the presence of catalytic amounts of metal ions such as iron, cobalt, nickel, molybdenum or vanadium ions—as well as transition metal oxides, such as for example manganese dioxide (manganese(IV) oxide) or cerium(IV) oxide.

For the oxidative polymerisation of thiophenes, there are theoretically required 2.25 equivalents of oxidising agent per mole of thiophene (see for example J. Polym. Sc. Part A Polymer Chemistry Vol. 26, p. 1287 (1988)). Smaller or larger amounts of equivalents of oxidising agent may however also be used.

The conducting polymers contained as solid electrolyte in the capacitors produced by the method according to the invention are cationic. In order to compensate the positive charge the cationic conducting polymers require anions as counter-ions.

Counter-ions may be monomeric or polymeric anions, the latter hereinafter being termed polyanions. Polymeric anions may for example be anions of polymeric carboxylic acids, such as polyacrylic acids, polymethacrylic acid or polymaleic acids, or polymeric sulfonic acids, such as polystyrenesulfonic acids and polyvinylsulfonic acids. These polycarboxylic and polysulfonic acids may also be copolymers of vinylcarboxylic acids and vinylsulfonic acids with other polymerisable monomers, such as acrylic acid esters and styrene.

Monomeric anions are preferably used for the solid electrolytes since they more readily penetrate the oxidised electrode body.

The following may for example serve as monomeric anions: monomeric anions of $C_1$-$C_{20}$-alkanesulfonic acids, such as methanesulfonic, ethanesulfonic, propanesulfonic, butanesulfonic or higher sulfonic acids such as dodecanesulfonic acid, of aliphatic perfluorosulfonic acids, such as trifluoromethanesulfonic acid, perfluorobutanesulfonic acid or perfluorooctanesulfonic acid, of aliphatic $C_1$-$C_{20}$-carboxylic acids such as 2-ethylhexylcarboxylic acid, of aliphatic perfluorocarboxylic acids such as trifluoroacetic acid or perfluorooctanoic acid, and of aromatic sulfonic acids optionally substituted by $C_1$-$C_{20}$-alkyl groups, such as benzenesulfonic acid, o-toluenesulfonic acid, p-toluenesulfonic acid or dodecylbenzenesulfonic acid, and of cycloalkanesulfonic acids such as camphorsulfonic acid, or tetrafluoroborates, hexafluorophosphates, perchlorates, hexafluoroantimonates, hexafluoroarsenates or hexachloroantimonates. The monomeric anions of sulfonic acids are not restricted to those of monosulfonic acids, but may also be anions of disulfonic, trisulfonic or polysulfonic acids, for example of benzenedisulfonic acid or naphthalenedisulfonic acid.

The anions of p-toluenesulfonic acid, methanesulfonic acid or camphorsulfonic acid are preferred.

The counter-anions are added preferably to the oxidizer or the stabilized monomer according to the present invention in the form of their alkali metal salts or as free acids.

The possibly present anions of the oxidising agent that is used may also serve as counter-ions, which means that it is not absolutely essential to add additional counter-ions.

As stated above, the precursor is coated with the monomer according to present invention, which in some cases can be provided in a solution and in other cases as such. The following organic solvents that are inert under the reaction conditions may in particular be mentioned as solvents for the monomer according to present invention for the production of conducting polymers and/or oxidising agents and/or counterions: aliphatic alcohols such as methanol, ethanol, i-propanol and butanol; aliphatic ketones such as acetone and methyl ethyl ketone; aliphatic carboxylic acid esters such as ethyl acetate and butyl acetate; aromatic hydrocarbons such as toluene and xylene; aliphatic hydrocarbons such as hexane, heptane and cyclohexane; chlorinated hydrocarbons such as dichloromethane and dichloroethane; aliphatic nitriles such as acetonitrile; aliphatic sulfoxides and sulfones such as dimethyl sulfoxide and sulfolane; aliphatic carboxylic acid amides such as methylacetamide, dimethylacetamide and dimethylformamide; aliphatic and araliphatic ethers such as diethyl ether and anisole. In addition water or a mixture of water with the aforementioned organic solvents may also be employed as solvent.

In the method according to the present invention it is further preferred that said adding comprises
coating said precursor with said monomer, preferably in form of a liquid phase such as a solution;
polymerizing said monomer such that the intrinsically conductive polymer is obtained.

The intrinsically conductive polymer can be added to the precursor by polymerisation of the monomer according to the present invention with oxidising agents or by electrochemical polymerisation of the monomer on the precursor. For the polymerisation of the monomer with oxidising agents, monomer and oxidizing agents can be applied as a mixture or successively to the precursor covered by a dielectric.

The oxidising agents and the monomer according to the present invention may be mixed together in solid and/or liquid form and then applied to the precursor to from the solid electrolyte layer. One or more solvents is/are however preferably added to the mixtures. As suitable solvents there may be mentioned in particular the solvents already listed above.

Oxidising agents and the monomer according to the present invention can also be applied successively, in some cases in the form of solutions, to the precursor for forming the solid electrolyte layer. When the monomer is applied first, it is preferred that the monomer is diluted with a solvent. As suitable solvents there may be mentioned in particular the solvents already listed above.

The monomer according to the present invention can also be electrochemically polymerized in the precursor for forming the solid electrolyte layer.

Oxidative polymerisation is carried out at temperatures from $-10°$ to $300°$ C., preferably $10°$ to $200°$ C., particularly preferably $30°$ to $150°$ C. The duration of the heat treatment depends on the nature of the polymer used for the coating and ranges from 5 seconds up to several hours. Temperature profiles with different temperatures and residence times may also be used for the thermal treatment.

It may be advantageous to wash out the excess oxidising agent and residual salts from the coating using a suitable solvent, preferably water or alcohols. Residual salts are understood in this connection to mean the reduced forms of the oxidising agent and possibly further salts that may be present.

For metal oxide dielectrics, such as for example oxides of valve metals, it may be advantageous to treat the oxide film electrochemically in order to rectify possible defects in the said oxide film and thereby reduce the residual current of the finished capacitor. In this so-called reforming the capacitor body is immersed in an electrolyte and a positive voltage is applied with positive potential to the electrode body. The electric current, which flows from the electrode body over defective sites in the oxide film to the conductive polymer, reforms the oxide film at these sites or destroys the conductivity of the conductive polymer at these defective sites.

Depending on the nature of the oxidised electrode body it may be advantageous to impregnate the oxidised electrode body before and/or after a wash procedure either one, two or several further times with the mixtures of the stabilized monomer according to the present invention and oxidising agents or successively with the monomer and oxidising agents in order to achieve thicker polymer layers in the interior of the electrode body. The compositions of the mixtures may in this connection vary. The solid electrolyte may optionally be composed of a multilayer system that comprises a plurality of functional layers.

The present invention also relates to a capacitor that has been manufactured by the method according to the present invention.

The capacitors manufactured in accordance with the invention are outstandingly suitable, owing to their low ESR, for use as a component in electronic circuits, for example as filter capacitors or decoupling capacitors. The use also forms part of the subject-matter of the invention. Preference is given to electronic circuits, as present, for example, in computers (desktops, laptops, servers), in computer peripherals (e.g. PC cards), in portable electronic devices, for example mobile phones, digital cameras or amusement electronics, in devices for amusement electronics, for example in CD/DVD players and computer game consoles, in navigation systems, in telecommunications equipment, in domestic appliances, in voltage supplies or in automotive electronics.

The present invention also relates to the use of the monomer according to the present invention for the manufacture of a capacitor, preferably an electronic capacitors. In this context preferred monomers and preferred capacitors are those which have been described above in connection with the monomer according to the present invention and in connection with the capacitors according to the present invention. One option in this context is again that the monomer according to the present invention is used as it is, i.e. with the colour numbers indicated above. It is especially preferred that the monomer, before it is used for the manufacture of the capacitor, is not purified in such a way that the Hazen or Gardner colour number is lowered.

The following FIGURE and the following examples serve for exemplary elucidation of the invention and are not to be interpreted as a restriction.

FIG. 1 shows the effect of the colour number of 3,4-ethylenedioxythiophen on the ESR of electronic capacitors that have been manufactures Using this monomer.

TEST METHODS

The colour was determined by the Hazen colour number for colours less than 1 Gardner colour number.

Determination of the Hazen Color Number

The determination of the color of the EDOT samples was based on the Pt—Co color value scale according to DIN EN ISO 6271-2:2002. As noted in here the terms Pt—Co color number and Hazen color numbers are equivalent.

A 2-channel spectrophotometer (Lambda 900, Perkin-Elmer) was used whose spectral accuracy is verified with the help of reference standards on a quarterly interval. The samples were measured with 50 mm rectangular cells (LZM130, Lange). The cells were fixed in a holder in the optical path for measurement, which had an aperture for the parallel optical path through the cell. All the spectral measurements were taken against air, i.e. the reference optical path was clear.

First, a background measurement was performed without the cell. Subsequently, the sample was filled in the cell, which was now in the measurement beam path. Only visually clear solutions were analyzed. The transmission spectrum of the solution was measured in the range of 400 nm-700 nm in 10 nm increments. The color coordinates were calculated according to Illuminant C (as defined in ASTM E308-94a) and a 2° observer according to DIN 5033. The derived chromaticity coordinate y was used to determine the Pt—Co color value.

Pt—Co solutions of different concentrations were prepared according to the DIN ISO EN 6271-1:2002. The Pt—Co solutions were measured under identical conditions as the EDOT samples and a calibration line of the Pt—Co color value and the chromaticity coordinate y was obtained. The Pt—Co color value which is identical to the Hazen color value was determined with this calibration line.

Determination of the Gardner Color Number

The determination of the color of EDOT samples was based on the Gardner color scale according to DIN EN ISO 4630-2:2002.

A 2-channel spectrophotometer (Lambda 900, Perkin-Elmer) was used whose spectral accuracy is verified with the help of reference standards on a quarterly interval. The samples were measured with 10 mm quadratic glass cells. The cells were fixed in a holder in the optical path for measurement, which had an aperture for the parallel optical path through the cell. All the spectral measurements were taken against air, i.e. the reference optical path was clear.

First, a background measurement was performed without the cell. Subsequently, the sample was filled in the cell, which was now in the measurement beam path. Only visually clear solutions were analyzed. The transmission spectrum of the solution was measured in the range of 400 nm-700 nm in 10 nm increments. The color coordinates were calculated according to illuminant C and a 2° observer according to DIN 5033. The derived chromaticity coordinates x and y and the tristimulus value Y were used to determine the Gardner color number according to DIN EN ISO 4630-1:2002.

EXAMPLES 3,4-ethylenedioxythiophene (EDOT) samples of different color numbers were prepared. As color numbers Hazen color and Gardner color numbers were used according to the above test methods.

1. Preparation of EDOT Samples

The Hazen respectively Gardner color number of freshly distilled EDOT (Clevios M V2, H. C. Starck Clevios GmbH) (sample A) with a purity higher than 99.9% and a EDOT (Clevios M V2, H. C. Starck Clevios GmbH) (sample X) which was aged over 4 years at room temperature in the dark were measured. Sample X was added to sample A until the Hazen respectively Gardner colour numbers given in the table below were obtained.

2. Production of Capacitors

Comparative Example 1

2.1 Production of Oxidised Electrode Pellets

Tantalum powder having a specific capacitance of 48,500 µFV/g (VFI50KD, H.C. Starck GmbH) was mixed with camphor as a binder and then compressed with a side press together with a tantalum anode wire of 0.49 mm diameter into porous electrode bodies (anode pellets) of dimension 4.4 mm×3.1 mm×1.0 mm. with a green density of 5.5 g/cm$^3$. The camphor binder was removed by a 90 min heat treatment at 190° C. Then the electrode pellets were sintered for 20 min at 1315° C. The pellets were anodised to 30 V in a phosphoric acid electrolyte of 4300 µS at 85° C. The current density was set to 150 mA per gram of used tantalum powder. After anodization the pellets were washed at 85° C. for 60 min and then dried.

2.2 Formation of Polymer Solid Electrolyte 2.2.1 A solution was prepared consisting of 1 part by weight of EDOT sample A and 20 parts by weight of a 40 wt. % ethanolic solution of iron(III) p-toluenesulfonate (Clevios C-E, H.C. Starck Clevios GmbH).

2.2.2 The solution was used to impregnate 9 anode pellets. The anode pellets were immersed in this solution with an automatic dip coater at a speed of. 0.3 mm/s and withdrawn form the solution with a speed of 1 mm/s after a soaking time of 60 s. Then the anodes pellets were exposed for 15 minutes at 25° C. to a relative atmospheric humidity of 95%.

2.2.3 Then process steps 2.2.1 and 2.2.2 were repeated on the anode pellets.

2.2.4 Following this the anodes pellets were heat treated for 30 minutes at 50° C. in a drying cabinet. The pellets were then washed for 60 minutes in an aqueous 2% solution of p-toluenesulfonic acid. The anode pellets were re-formed at 30 V for 30 minutes in a aqueous solution of p-toluenesulfonic acid of 4300 µS at 25° C., and then rinsed in distilled water and dried.

2.2.5 The process steps 2.2.1 to 2.2.4 were repeated two times.

2.3 Formation of Outer Coatings and Electrical Measurement 868 g deionised water, 330 g of an aqueous polystyrene sulphuric acid solution having an average molecular weight of 70,000 and a solids content of 3.8% by weight were placed in a 2-1 three-necked flask with stirrer and internal thermometer. The reaction temperature was maintained between 20 and 25° C. 5.1 g 3,4-ethylenedioxythiophene were added while stirring. The solution was stirred for 30 minutes. 0.03 g iron(III) sulphate and 9.5 g sodium persulphate were then added and the solution was stirred for a further 24 hours, Once the reaction has been completed, 100 ml of a strongly acid cation exchanger and 250 ml of a weakly basic anion exchanger were added, for removing inorganic salts, and the solution was stirred for a further two hours. The ion exchanger was filtered out and a poly(3,4-ethylenedioxythiophene)/polystyrene sulphonate dispersion was obtained.

2.5 l demineralised water were placed in a 5-1 glass reactor with stirrer and thermometer. 214.2 g p-toluene sulphonic acid monohydrate and 2.25 g iron(III) sulphate heptahydrate were introduced while stirring. Once the entire mixture had dissolved, 85.8 g 3,4-ethylenedioxythiophene were added and stirring was continued for 30 minutes. 192.9 g sodium persulphate were then introduced while stirring, and the mixture was stirred for a further 24 hours at ambient temperature. After the end of the reaction, the PEDT/toluene sulphonate powder was filtered out on a porcelain suction filter, washed with 3 l demineralised water and finally dried for 6 hours at 100° C. 89 g of a bluish black PEDT toluene sulphonate powder were obtained.

In a beaker with stirrer, 170 g of the poly(3,4-ethylenedioxythiophene)/polystyrene sulphonate dispersion, 15 g of a waterbased polyester dispersion, 8 g dimethyl sulphoxide, 1 g 3-glycidoxypropyltrimethoxysilane and 0.4 g of a non-ionic acetylenic-based wetting agent were mixed intensively for one hour. 6 g of the PEDT/toluene sulphonate powder were then dispersed using a bead mill dissolver unit. For this purpose, 300 g of zirconium oxide beads (Ø 1 mm) were added and the mixture was stirred at 7000 rpm for one hour, while being cooled with water. Finally, the ground beads were separated via a 0.8 µm sieve.

The anode pellets which were prepared according to section 2.1 and 2.2 were then dipped in the so prepared dispersion and subsequently dried for 10 min at 120° C. The dipping into the dispersion was carried out with an automatic dip coater at a speed of 0.15 mm/s. The anode pellets were withdrawn form the dispersion with a speed of 1 mm/s after a soaking time of 10 s.

Afterwards the pellets were dip-coated with a graphite (mixture of 1 part by weight Electrodag PR406 (Acheson) and 3 parts by weight diethylene glycol butyl ether (Aldrich)) and dried for 30 min at 25° C., 30 min at 50° C. and 15 min at 150° C. The pellets were then dip-coated with a silver (Electrodag 503, Acheson) and dried for 15 min at 25° C. and 45 min at 150° C.

The capacitance was determined at 120 Hz and the equivalent series resistance (ESR) at 100 kHz using a LCR meter (Agilent 4284A) with a four-point probe. The average electrical results of the 9 capacitors are given in Table 1. The standard deviation of the average was 0.5% for capacitance and 1 mΩ for ESR.

3. Examples 1 to 16 and Comparative Examples 2 to 8

23 further sets of nine capacitors each were produced and measured analogously to Comparative Example 1 but instead of using EDOT sample A for the formation of the polymer solid electrolyte EDOT samples B (example 2) to X (comparative example 8) were used.

The average electrical results of the nine capacitors for each example are given in the following table. The standard deviation of the average was 0.5% for capacitance and 1 mΩ for ESR.

The results are also illustrated in FIG. 1.

As can be seen from the results shown in the table and FIG. 1, low ESR-values in combination with high values for the capacitance of capacitors based on poly(3,4-ethylenedioxythiophene) as electrically conductive polymer material can be obtained in a reproducible manner of the monomer is characterized by a Hazen colour number of at least 20 and a Gardner colour number of not more than 5.

TABLE 1

| Example/Comparative Example | Sample | Colour index | Colour number | Capacitance [μF] | ESR [mΩ] |
|---|---|---|---|---|---|
| Comp. 1 | A | Hazen | 5 | 89 | 25 |
| Comp. 2 | B | Hazen | 10 | 89 | 25 |
| Comp. 3 | C | Hazen | 15 | 89 | 25 |
| Ex. 1 | D | Hazen | 20 | 89 | 21 |
| Ex. 2 | E | Hazen | 25 | 89 | 19 |
| Ex. 3 | F | Hazen | 30 | 90 | 14 |
| Ex. 4 | G | Hazen | 40 | 90 | 13 |
| Ex. 5 | H | Hazen | 50 | 90 | 12 |
| Ex. 6 | I | Hazen | 60 | 90 | 12 |
| Ex. 7 | J | Hazen | 80 | 90 | 12 |
| Ex. 8 | K | Hazen | 100 | 90 | 12 |
| Ex. 9 | L | Hazen | 125 | 90 | 12 |
| Ex. 10 | M | Hazen | 175 | 90 | 12 |
| Ex. 11 | N | Hazen | 200 | 90 | 12 |
| Ex. 12 | O | Gardner | 1 | 90 | 14 |
| Ex. 13 | P | Gardner | 2 | 89 | 15 |
| Ex. 14 | Q | Gardner | 3 | 89 | 17 |
| Ex. 15 | R | Gardner | 4 | 89 | 19 |
| Ex. 16 | S | Gardner | 5 | 89 | 21 |
| Comp. 4 | T | Gardner | 6 | 89 | 23 |
| Comp. 5 | U | Gardner | 8 | 85 | 25 |
| Comp. 6 | V | Gardner | 10 | 84 | 25 |
| Comp. 7 | W | Gardner | 12 | 80 | 27 |
| Comp. 8 | X | Gardner | 15 | 79 | 27 |

Example 17

A porous aluminium foil which had been anodized to 92 V and is of dimensions 170 mm×5 mm (anode foil) and a porous aluminium foil of dimensions 200 mm×5 mm (cathode foil) were each provided with a contact wire, then wound together with two cellulose separator papers separating both aluminium foils and fixed with adhesive tape. 9 of these oxidized electrode bodies were produced. The separator paper of the oxidized electrode bodies was then carbonized in an oven at 300° C.

The oxidized electrode bodies were dipped in a 40 wt. % butanolic solution of iron(III) p-toluenesulfonate (Clevios C-B 40 V2, H.C. Starck Clevios GmbH) for 60 s and then dried for 15 min at 50° C., 15 min at 100° C. and 30 min at 150° C. The oxidized electrode bodies were then dipped in EDOT sample 0 for 30 s and then dried for 15 min at 25° C., 15 min at 50° C. and 30 min at 120° C. The capacitance was determined at 120 Hz and the equivalent series resistance (ESR) at 100 kHz using a LCR meter (Agilent 4284A) with a four-point probe. The average electrical results of the 9 capacitors are given in Table 2.

Comparative Example 9

9 capacitors were produced and measured analogously to Example 17 but instead of using EDOT sample 0 for the formation of the polymer solid electrolyte EDOT sample V was used. The average electrical results of the 9 capacitors for each example are given in Table 2.

TABLE 2

| Example | Sample | Colour index | Colour number | Capacitance [μF] | ESR [mΩ] |
|---|---|---|---|---|---|
| 17 | O | Gardner | 1 | 98 | 27 |
| Comp. 9 | V | Gardner | 10 | 92 | 45 |

The invention claimed is:

1. A monomer having the general formula (I):

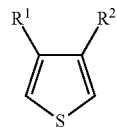

(I)

wherein $R^1$ and $R^2$ each independently represent for hydrogen, for an optionally substituted $C_1$-$C_{20}$-alkyl group or $C_1$-$C_{20}$-oxyalkyl group, optionally interrupted by 1 to 5 oxygen atoms and/or sulfur atoms, or jointly for an optionally substituted $C_1$-$C_{20}$-dioxyalkylene group or $C_6$-$C_{20}$-dioxyarylene group,
wherein the monomer has a colour in a range of
a Hazen colour number determined according to test method described herein of at least 20,
to
a Gardner colour number determined according to test method described herein of not more than 5.

2. The monomer according to claim 1, wherein the thiophene derivative monomers are those having the general formula (II)

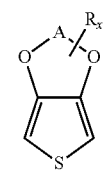

(II)

in which
A stands for an optionally substituted $C_1$-$C_5$-alkylene residue or a $C_6$-$C_{14}$-arylene residue,
R stands for a linear or branched, optionally substituted $C_1$-$C_{18}$-alkyl residue, preferably a linear or branched, optionally substituted $C_1$-$C_{14}$-alkyl residue, an optionally substituted $C_5$-$C_{12}$-cycloalkyl residue, an optionally substituted $C_6$-$C_{14}$-aryl residue, an optionally substituted $C_7$-$C_{18}$-aralkyl residue, an optionally substituted C1-C4-hydroxyalkyl residue, or a hydroxyl residue,
x stands for an integer from 0 to 8 and
in the case where several residues R are bonded to A, these may be the same or different.

3. The monomer according to claim 1, wherein the thiophene derivative monomers are those having the general formula (IIa)

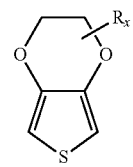

(IIa)

in which R and x have the significance stated in claim 1.

4. The monomer according to claim 1, wherein the thiophene derivative monomer is 3,4-ethylenedioxythiophene.

5. The monomer according to claim 1, wherein the range is from a Hazen colour number determined according to the test method described herein of at least 25 to a Gardner colour number determined according to the test method described herein of not more than 4.

6. The monomer according to claim 1,
wherein the range is from a Hazen colour number determined according to the test method described herein of at least 30 to a Gardner colour number determined according the test method described herein of not more than 3.

7. The monomer according to claim 1, wherein the range is from Hazen colour number determined according to the test method described herein of at least 30 to a Gardner colour number determined according to the test method described herein of not more than 2.

8. The monomer according to claim 1, wherein the range is from Hazen colour number determined according to the test method described herein of at least 30 to a Gardner colour number determined according to the test method described herein of not more than 1.

9. The monomer according to claim 1, wherein the range is form a Hazen colour number determined according to the test method described herein of at least 50 to of not more than 200.

10. A method for the manufacture of a capacitor comprising
forming an anode of a valve metal;
forming a precursor comprising said anode and a dielectric;
adding an intrinsically conductive polymer on said precursor, wherein said intrinsically conductive polymer is based on the monomer as defined in claim 1.

11. The method according to claim 10, wherein said adding comprises
coating said precursor with said monomer;
polymerizing said monomer such that the intrinsically conductive polymer is obtained.

12. A capacitor, obtainable by the method according to claim 11.

13. Use of a monomer as defined in claim 1 for the manufacture of a capacitor.

14. The monomer according to claim 1, wherein the thiophene derivative monomers are those having the general formula (II)

(II)

in which
A stands for an optionally substituted $C_1$-$C_5$-alkylene residue or a an optionally substituted $C_2$-$C_3$- alkylene residue,
R stands for a linear or branched, optionally substituted $C_1$-$C_{14}$-alkyl residue, preferably a linear or branched, optionally substituted $C_1$-$C_{14}$-alkyl residue, an optionally substituted $C_5$-$C_{12}$-cycloalkyl residue, an optionally substituted $C_6$-$C_{14}$-aryl residue, an optionally substituted $C_7$-$C_{18}$-aralkyl residue, an optionally substituted $C_1$-$C_2$-hydroxyalkyl residue, or a hydroxyl residue,
x stands for an integer from 0 to 6, and in the case where several residues R are bonded to A, these may be the same or different.

15. The monomer according to claim 14, wherein x stands for an integer 0 or 1.

16. A process for the manufacture of a capacitor which comprises utilizing the monomer as defined in claim 1.

* * * * *